(12) United States Patent
Morichika et al.

(10) Patent No.: US 9,084,777 B2
(45) Date of Patent: Jul. 21, 2015

(54) STABILIZED ANTIBODY-CONTAINING FORMULATIONS

(75) Inventors: Toshiyuki Morichika, Tokyo (JP); Daisuke Kameoka, Tokyo (JP)

(73) Assignee: CHUGAI SEIYAKU KABUSHIKI KAISHA, Tokyo (JP)

( * ) Notice: Subject to any disclaimer, the term of this patent is extended or adjusted under 35 U.S.C. 154(b) by 630 days.

(21) Appl. No.: 12/159,778

(22) PCT Filed: Dec. 27, 2006

(86) PCT No.: PCT/JP2006/326121
§ 371 (c)(1), (2), (4) Date: Jun. 30, 2008

(87) PCT Pub. No.: WO2007/074880
PCT Pub. Date: Jul. 5, 2007

(65) Prior Publication Data
US 2009/0291076 A1    Nov. 26, 2009

(51) Int. Cl.
| A61K 39/00 | (2006.01) |
| A61K 39/395 | (2006.01) |
| C07K 16/00 | (2006.01) |
| A61K 9/19 | (2006.01) |
| A61K 47/18 | (2006.01) |
| C07K 16/28 | (2006.01) |
| A61K 9/00 | (2006.01) |

(52) U.S. Cl.
CPC ............ *A61K 39/39591* (2013.01); *A61K 9/19* (2013.01); *A61K 47/183* (2013.01); *C07K 16/2866* (2013.01); *A61K 9/0019* (2013.01); *A61K 2039/505* (2013.01); *C07K 2317/24* (2013.01)

(58) Field of Classification Search
None
See application file for complete search history.

(56) References Cited

U.S. PATENT DOCUMENTS

| 5,908,826 A | 6/1999 | Fukuda et al. | |
| 6,875,432 B2 * | 4/2005 | Liu et al. | 424/130.1 |
| 6,887,852 B1 | 5/2005 | Paik et al. | |
| 2001/0014326 A1 * | 8/2001 | Andya et al. | 424/130.1 |
| 2002/0045571 A1 | 4/2002 | Liu et al. | |
| 2004/0115197 A1 * | 6/2004 | Yoshizaki et al. | 424/145.1 |
| 2005/0118163 A1 | 6/2005 | Mizushima et al. | |

FOREIGN PATENT DOCUMENTS

| EP | 0 5310539 A1 | 3/2003 |
| EP | 1 475 100 A1 | 11/2004 |
| JP | 55-164630 A | 12/1980 |
| JP | 11-080022 A | 3/1999 |
| WO | 0230463 A2 | 4/2002 |

OTHER PUBLICATIONS

Chen, 2003, Pharmaceutical Research, vol. 20, Issue 12, pp. 1952-1960.*
Mattern, et al "Formulation of Proteins in Vacuum-Dried Glasses. II. Process and Storage Stability in Sugar-Free Amino Acid Systems," Pharmaceutical Development and Technology, 4(2): 199-208 (1999).
Search report in co-pending European Patent Appln No. 06843503.1 dated May 6, 2010.

* cited by examiner

*Primary Examiner* — Elizabeth C Kemmerer
(74) *Attorney, Agent, or Firm* — Browdy and Neimark, PLLC

(57) ABSTRACT

The present invention relates to antibody-containing lyophilized formulations free from reducing sugars, non-reducing sugars, sugar alcohols or polysaccharides as excipients and including one or more amino acid selected from the group consisting of arginine, histidine, lysine, serine, proline, glycine, alanine and threonine or a salt thereof.

6 Claims, No Drawings

US 9,084,777 B2

STABILIZED ANTIBODY-CONTAINING FORMULATIONS

TECHNICAL FIELD

The present invention relates to antibody-containing formulations, especially stable high-concentration lyophilized antibody formulations.

BACKGROUND ART

With the development of genetic recombination technology, various protein formulations became supplied in stable amounts. To ensure stability, these formulations are supplied in the dosage form of a lyophilized protein ingredient powder to be dissolved just before use in a separately packaged water-soluble diluent or in the dosage form of a protein solution formulation containing additives for improving stability.

Recently, various antibody formulations have been developed and applied for practical use, but many of the antibody formulations are used as formulations for intravenous injection. However, there are increasing demands in the medical field for developing antibody-containing formulations in the form of self-injectable formulations for subcutaneous injection.

In designing antibody-containing formulations for subcutaneous injection, the antibody concentration in the solution to be administered must be high because the injectable volume by subcutaneous injection is normally limited despite of a single high antibody dose (about 100-200 mg). Thus, there are demands for developing high-concentration antibody-containing formulations by means of lyophilization-based concentration.

JPA No. 2004-532798/WO 2002/030463/U.S. Pat. No. 6,875,432 discloses a concentrated protein formulation with decreased viscosity including a salt and/or a buffer, but describes only the effect of reducing the viscosity of the solution and nothing about stability.

JPA No. 2004-538287/WO 2003/009817 discloses a lyophilized pharmaceutical formulation prepared by lyophilizing an aqueous preparation containing an IgG antibody at a high concentration, Polysorbate, sucrose, and optionally serine and/or mannitol in a histidine buffer (pH about 5.5 to about 6.5). However, this application focuses on the stabilizing effect of sucrose, but describes nothing about the stabilizing effect by adding serine and histidine.

High-concentration antibody-containing solutions tend to form high-viscosity solutions by the properties of proteins as macromolecules and molecular interactions. Moreover, they are normally lyophilized in the presence of large amounts of lyoprotectants such as sugars during the preparation of lyophilized formulations to maintain their caking properties and stability. However, sugars enhance molecular interactions to increase viscosity, and the resulting high-viscosity formulations are difficult to dispense, draw into syringes and subcutaneously inject. Thus, novel methods for preparing stable lyophilized formulations without adding sugars are needed.

DISCLOSURE OF THE INVENTION

Problems to be Solved by the Invention

An object of the present invention is to provide a stable antibody formulation that forms little dimers or low molecular weight degradation products of the antibody during the process of preparing a high-concentration antibody-containing formulation by means of lyophilization-based concentration without adding sugars and during storage and reconstitution of the resulting high-concentration lyophilized formulation.

Means of Solving the Problems

As a result of careful studies to attain the above object, we accomplished the present invention on the basis of the finding that high-concentration antibody-containing lyophilized formulations can be obtained without adding sugars as fillers by adding one or more amino acid selected from the group consisting of arginine, histidine, lysine, serine, proline, glycine, alanine and threonine or a salt thereof.

Accordingly, the present invention provides the following:

(1) An antibody-containing lyophilized formulation free from reducing sugars, non-reducing sugars, sugar alcohols or polysaccharides as fillers and including one or more amino acid selected from the group consisting of arginine, histidine, lysine, serine, proline, glycine, alanine and threonine or a salt thereof.

(2) The formulation as defined in (1) wherein the antibody concentration of the lyophilized formulation after reconstitution is 10 mg/mL or more.

(3) The formulation as defined in (2) wherein the antibody concentration of the lyophilized formulation after reconstitution is 50 mg/mL or more.

(4) The formulation as defined in (3) wherein the antibody concentration of the lyophilized formulation after reconstitution is 100 mg/mL or more.

(5) The formulation as defined in any one of (1) to (4) wherein the content of the amino acid or a salt thereof is 270 moles or more per mole of the antibody.

(6) The formulation as defined in (5) wherein the content of the amino acid or a salt thereof is 380 moles or more per mole of the antibody.

(7) The formulation as defined in (6) wherein the content of the amino acid or a salt thereof is 540 moles or more per mole of the antibody.

(8) The formulation as defined in any one of (1) to (7) wherein the pH of the solution after reconstitution is 4-8.

(9) The formulation as defined in (8) wherein the pH of the solution after reconstitution is 5.0-7.5.

(10) The formulation as defined in any one of (1) to (9) wherein the antibody is a chimeric antibody, humanized antibody or human antibody.

(11) The formulation as defined in (10) wherein the antibody is an anti-IL-6 receptor antibody.

(12) The formulation as defined in any one of (1) to (11) wherein the amino acid or a salt thereof is one or more amino acid selected from the group consisting of arginine, histidine and lysine or a salt thereof.

(13) The formulation as defined in (12) wherein the amino acid or a salt thereof is arginine or a salt thereof.

(14) The formulation as defined in any one of (1) to (13) wherein the viscosity after reconstitution is 20 mPa·s or less.

(15) The formulation as defined in (14) wherein the viscosity after reconstitution is 15 mPa·s or less.

(16) The formulation as defined in (15) wherein the viscosity after reconstitution is 12 mPa·s or less.

(17) An antibody-containing lyophilized formulation including one or more amino acid selected from the group consisting of arginine, histidine, lysine, serine, proline, glycine, alanine and threonine or a salt thereof as a lyoprotectant or a filler characterized in that it includes 25 mg/ml or more of the amino acid or a salt thereof when the antibody concentration of the lyophilized formulation is 20 mg/mL or more, or it includes 12.5 mg/ml or more of the amino acid or a salt thereof when the antibody concentration is 30 mg/mL or more, or it includes 6.25 mg/ml or more of the amino acid or a salt thereof when the antibody concentration is 40 mg/mL or more.

(18) The formulation as defined in (17) characterized in that it includes 25 mg/ml or more of the amino acid or a salt thereof when the antibody concentration of the lyophilized formulation is 30 mg/mL or more, or it includes 12.5 mg/ml or more of the amino acid or a salt thereof when the antibody concentration is 40 mg/mL or more.

(19) A process for preparing an antibody-containing lyophilized formulation including one or more amino acid selected from the group consisting of arginine, histidine, lysine, serine, proline, glycine, alanine and threonine or a salt thereof as a lyoprotectant or a filler, comprising the step of lyophilizing a solution before lyophilization having a total concentration of reducing sugars, non-reducing sugars, sugar alcohols and polysaccharides of less than 20 mg/mL.

(20) An antibody-containing lyophilized formulation including one or more amino acid selected from the group consisting of arginine, histidine, lysine, serine, proline, glycine, alanine and threonine or a salt thereof as a lyoprotectant or a filler, wherein the ratio per vial of antibody weight to the total weight of reducing sugars, non-reducing sugars, sugar alcohols and polysaccharides is less than 1:0.5.

(21) A protein-containing lyophilized formulation free from reducing sugars, non-reducing sugars, sugar alcohols or polysaccharides as fillers and including one or more amino acid selected from the group consisting of arginine, histidine, lysine, serine, proline, glycine, alanine and threonine or a salt thereof.

(22) A process for preparing a protein-containing lyophilized formulation including one or more amino acid selected from the group consisting of arginine, histidine, lysine, serine, proline, glycine, alanine and threonine or a salt thereof as a lyoprotectant or a filler, comprising the step of lyophilizing a solution before lyophilization having a total concentration of reducing sugars, non-reducing sugars, sugar alcohols and polysaccharides of less than 20 mg/mL.

(23) A protein-containing lyophilized formulation including one or more amino acid selected from the group consisting of arginine, histidine, lysine, serine, proline, glycine, alanine and threonine or a salt thereof as a lyoprotectant or a filler, wherein the ratio per vial of protein weight to the total weight of reducing sugars, non-reducing sugars, sugar alcohols and polysaccharides is less than 1:0.5.

The Most Preferred Embodiments of the Invention

Antibodies used in the methods of the present invention are not specifically limited so far as they bind to a desired antigen, and may be polyclonal or monoclonal, but preferably monoclonal because homogeneous antibodies can be stably produced.

Monoclonal antibodies used in the present invention include not only monoclonal antibodies derived from animals such as humans, mice, rats, hamsters, rabbits, sheep, camels and monkeys but also artificially modified recombinant antibodies such as chimeric antibodies, humanized antibodies and bispecific antibodies. The antibodies may belong to any immunoglobulin class including, but not limited to, IgG such as IgG1, IgG2, IgG3 or IgG4, and IgA, IgD, IgE and IgM, preferably IgG and IgM.

Moreover, the antibodies of the present invention include not only whole antibodies, but also antibody fragments such as Fv, Fab and F(ab)$_2$ or fragmented antibodies such as monovalent or multivalent single chain Fvs (scFv, sc(Fv)$_2$ and diabodies such as scFv dimers) in which the variable regions of an antibody are joined together via a linker such as a peptide linker.

The antibodies of the present invention described above can be prepared by processes well known to those skilled in the art.

Hybridomas producing monoclonal antibodies can be basically constructed by known techniques as follows. That is, a desired antigen or a cell expressing a desired antigen is used as an immunizing antigen to immunize host cells according to a standard immunization technique, and the resulting immunized cells are fused to known parent cells by a standard cell fusion technique, and then the fused cells are screened for monoclonal antibody-producing cells (hybridomas) by a standard screening method. Construction of hybridomas can be performed according to the method of e.g. Milstein et al. (Kohler. G. and Milstein, C., Methods Enzymol. (1981) 73: 3-46). If the antigen has low immunogenicity, it can be bound to an immunogenic macromolecule such as albumin and used for immunization.

Recombinant antibodies can be used, which are produced by transforming a host with a suitable vector containing an antibody gene cloned from a hybridoma using genetic engineering techniques (e.g., see Carl, A. K. Borrebaeck, James, W. Larrick, THERAPEUTIC MONOCLONAL ANTIBODIES, Published in the United Kingdom by MACMILLAN PUBLISHERS LTD, 1990). Specifically, the cDNA sequences for the variable regions (V regions) of an antibody are synthesized from mRNA of a hybridoma using a reverse transcriptase. Thus obtained DNA sequences encoding the V regions of the desired antibody are linked to the DNA sequences encoding the constant regions (C regions) of the desired antibody and integrated into an expression vector. Alternatively, the DNA sequences encoding the V regions of the antibody can be integrated into an expression vector containing the DNA sequences for the C regions of the antibody. They are integrated into the expression vector in such a manner that they can be expressed under the control of regulatory regions such as enhancers and promoters. Then, a host cell can be transformed with this expression vector to express the antibody.

In the present invention, recombinant antibodies, i.e. antibodies artificially modified to reduce antigenicity in humans or to attain other purposes, such as chimeric antibodies and humanized antibodies can be used. These modified antibodies can be prepared by known processes. Chimeric antibodies consist of the heavy and light chain variable regions of an antibody from a non-human mammal such as a mouse and the heavy and light chain constant regions of a human antibody and can be obtained by linking the DNA sequences encoding the variable regions of the mouse antibody to the DNA sequences for the constant regions of the human antibody and transforming a host with an expression vector containing the linked sequences to allow it to produce a chimeric antibody.

Humanized antibodies are also called reshaped human antibodies and obtained by grafting the complementarity-determining regions (CDRs) of an antibody from a non-human mammal such as a mouse into the complementarity-determining regions of a human antibody and typical gene recombination techniques for preparing them are also known. Specifically, DNA sequences designed to link the CDRs of a mouse antibody to the framework regions (FRs) of a human antibody are synthesized by PCR from several oligonucleotides prepared to have terminal overlapping regions. The resulting DNA sequences are linked to the DNA sequences encoding the constant regions of the human antibody and then integrated into an expression vector, which is transformed into a host to allow it to produce a reshaped antibody (see European Patent Publication No. EP 239400, International Publication No. WO 96/02576). The FRs of the human antibody linked by the CDRs are selected in such a manner that the complementarity-determining regions form an appropriate antigen-binding site. If necessary, reshaped human antibodies may have some amino acid changes in the framework regions of the variable regions so that the complementarity-determining regions form an appropriate antigen-binding site (Sato, K. et al., Cancer Res. (1993) 53, 851-856).

Methods for obtaining human antibodies are also known. For example, a desired human antibody having a binding activity for a desired antigen can be obtained by in vitro immunizing human lymphocytes with the desired antigen or a cell expressing the desired antigen and fusing the immunized lymphocytes to human myeloma cells such as U266 (see JPB No. HEI-1-59878). A desired human antibody can also be obtained by immunizing a transgenic animal having all human antibody gene repertoires with an antigen (see International Publications Nos. WO 93/12227, WO 92/03918, WO 94/02602, WO 94/25585, WO 96/34096, WO 96/33735). Methods for obtaining a human antibody by panning using a human antibody library are also known. For example, phages binding to an antigen can be selected by expressing the variable regions of a human antibody as single chain antibody fragments (scFv) on phage surfaces by a phage display method. The DNA sequences encoding the variable regions of the human antibody binding to the antigen can be determined by analyzing the genes of the selected phages. A whole human antibody can be obtained by preparing a suitable expression vector containing the determined DNA sequences of the scFv fragments binding to the antigen. These methods have already been well known from WO 92/01047, WO 92/20791, WO 93/06213, WO 93/11236, WO 93/19172, WO 95/01438, WO 95/15388.

When an antibody is to be prepared by transforming a preliminarily isolated antibody gene into a suitable host, a combination of the suitable host with an expression vector can be used. Suitable eukaryotic cells for use as hosts include animal, plant and fungal cells. Known animal cells include (1) mammal cells such as CHO, COS, myeloma, BHK (baby hamster kidney), HeLa and Vero cells; (2) amphibian cells such as *Xenopus* oocytes; or (3) insect sells such as sf9, sf21 and Tn5. Known plant cells include cells of *Nicotiana* such as *Nicotiana tabacum*, which can be used as callus cultures. Known fungi include yeasts such as *Saccharomyces* spp., e.g. *Saccharomyces serevisiae* and filamentous fungi such as *Aspergillus* spp., e.g. *Aspergillus niger*. Prokaryotic cells can be used as producing systems using bacterial cells. Known bacterial cells include *E. coli* and *Bacillus subtilis*. Antibodies can be obtained by transforming these cells with an antibody gene of interest and culturing the transformed cells in vitro.

Moreover, the antibodies of the present invention may be antibody fragments or fragmented antibodies and modified antibodies. For example, antibody fragments or fragmented antibodies include Fab, (Fab')$_2$, Fv, or single chain Fvs (scFv, sc(Fv)$_2$, etc.) in which the heavy and light chain Fv fragments are joined via a suitable linker (Huston, J. S. et al., Proc. Natl. Acad. Sci. U.S.A. (1988) 85, 5879-5883). Specifically, an antibody is treated with an enzyme such as papain or pepsin to produce antibody fragments or the genes encoding these antibody fragments are constructed and introduced into an expression vector and then expressed in a suitable host cell (e.g., see Co, M. S. et al., J. Immunol. (1994) 152, 2968-2976; Better, M. and Horwitz, A. H., Methods Enzymol. (1989) 178, 476-496; Pluckthun, A. and Skerra, A., Methods Enzymol. (1989) 178, 497-515; Lamoyi, E., Methods Enzymol. (1986) 121, 652-663; Rousseaux, J. et al., Methods Enzymol. (1986) 121, 663-669; Bird, R. E. and Walker, B. W., Trends Biotechnol. (1991) 9, 132-137).

Modified antibodies including antibodies conjugated with various molecules such as polyethylene glycol (PEG) can also be used. These modified antibodies are also included in the "antibodies" of the present invention. Such modified antibodies can be obtained by chemically modifying the antibodies produced as above. These methods have already been established in this field of art.

Antibodies contained in the formulations of the present invention include, but not limited to, anti-tissue factor antibodies, anti-IL-6 receptor antibodies, anti-HM1.24 antigen monoclonal antibodies, anti-parathyroid hormone related peptide antibodies (anti-PTHrP antibodies), anti-glypican-3 antibodies, anti-ganglioside GM3 antibodies, anti-TPO receptor agonist antibodies, alternative antibodies to coagulation VIII factor, etc.

Preferred reshaped humanized antibodies for use in the present invention include humanized anti-IL-6 receptor antibodies (hPM-1) (see International Publication No. WO92-19759), humanized anti-HM1.24 antigen monoclonal antibodies (see International Publication No. WO98-14580), humanized anti-parathyroid hormone related peptide antibodies (anti-PTHrP antibodies) (see International Publication No. WO98-13388), humanized anti-tissue factor antibodies (see International Publication No. WO99-51743), and humanized anti-glypican-3 IgG1K antibodies (see International Application No. PCT/JP05/013103). Especially preferred humanized antibodies for use in the present invention are humanized anti-IL-6 receptor antibodies.

Preferred human IgM antibodies include recombinant human IgM anti-ganglioside GM3 antibodies (see International Publication No. WO05-05636).

Preferred fragmented antibodies include anti-TPO receptor diabodies (see International Publication No. WO02-33072) and anti-CD47 agonist diabodies (see International Publication No. WO01-66737).

The antibody-containing lyophilized formulations of the present invention preferably have an antibody concentration of 10 mg/mL or more, more preferably 50 mg/mL or more, still more preferably 80 mg/mL or more, especially 100 mg/mL or more after the lyophilized formulations are reconstituted.

The antibody-containing lyophilized formulations of the present invention may have any antibody concentration before lyophilization. However, when a high-concentration solution formulation is prepared by reconstituting a lyophilized formulation with a smaller volume of water than contained in the solution before lyophilization, i.e. when the so-called lyophilization-based concentration technique is applied, the antibody concentration before lyophilization is preferably 1 mg/mL or more, more preferably 10 mg/mL or more, especially 20 mg/mL or more. The concentration factor of the antibodies in the lyophilization-based concentration technique is preferably 2- to 50-fold, more preferably 2- to 20-fold, especially 2- to 6-fold.

The amino acid added as a stabilizer to the formulations of the present invention is an amino acid selected from the group consisting of arginine, histidine, lysine, serine, proline, glycine, alanine and threonine and salts thereof, preferably an amino acid selected from the group consisting of L-arginine, L-histidine, L-lysine, L-serine, L-proline, glycine, L-alanine and L-threonine and salts thereof. An especially preferred amino acid is L-arginine or a salt thereof.

The content of the amino acid in the formulations of the present invention is preferably 270 moles or more per mole of the antibody, more preferably 380 moles or more per mole of the antibody, still more preferably 540 moles or more per mole of the antibody.

In the high-concentration antibody-containing lyophilized formulations of the present invention, the pH of the solution after reconstitution of the lyophilized formulations is preferably 4-8, more preferably 5.0-7.5, still more preferably 5.5-7.2.

In the formulations of the present invention, the viscosity after reconstitution is preferably 20 mPa·s or less, more preferably 15 mPa·s or less, still more preferably 12 mPa·s or less.

The formulations of the present invention are characterized in that they are free from reducing sugars, non-reducing sugars, sugar alcohols or polysaccharides as fillers. Normally, when reducing sugars, non-reducing sugars, sugar alcohols or polysaccharides are added to protein-containing formulations as fillers for lyophilized formulations, they should be included at a level of 20 mg/mL or more in a solution before lyophilization. Thus, the expression "free from reducing sugars, non-reducing sugars, sugar alcohols or polysaccharides as fillers" as used herein means that the total concentration of reducing sugars, non-reducing sugars, sugar alcohols or polysaccharides included in a solution before lyophilization during the preparation of a protein-containing lyophilized formulation is less than 20 mg/mL, preferably 10 mg/mL or less, more preferably 5 mg/mL or less, still more preferably 1 mg/mL or less, especially substantially zero.

The present invention also provides an antibody-containing lyophilized formulation including one or more amino acid selected from the group consisting of arginine, histidine, lysine, serine, proline, glycine, alanine and threonine or a salt thereof as a lyoprotectant or a filler, wherein the ratio per vial of antibody weight to the total weight of reducing sugars, non-reducing sugars, sugar alcohols and polysaccharides is less than 1:0.5. The ratio per vial of antibody weight to the total weight of reducing sugars, non-reducing sugars, sugar alcohols and polysaccharides is preferably less than 1:0.5, more preferably 1:0.25 or less, still more preferably 1:0.125 or less, even still more preferably 1:0.025 or less, and most preferably the formulation is free from reducing sugars, non-reducing sugars, sugar alcohols and polysaccharides.

As used herein, the reducing sugars include glucose, fructose, maltose, lactose; the non-reducing sugars include sucrose, trehalose, raffinose, neotrehalose; the sugar alcohols include mannitol, sorbitol, maltitol, erythritol; and the polysaccharides include dextran, cyclodextrins α-cyclodextrin, β-cyclodextrin, γ-cyclodextrin), carboxymethyl cellulose, hydroxypropylmethyl cellulose.

The formulations of the present invention can form stable antibody formulations that ensure good caking and form little dimers or low molecular weight degradation products of the antibody during the lyophilization process and during storage and reconstitution of the lyophilized formulations without adding reducing sugars, non-reducing sugars, sugar alcohols or polysaccharides as fillers. Moreover, easy-to-use lyophilized formulations can be obtained in which the increase of the viscosity of the high-concentration antibody-containing solution after reconstitution can be prevented because they contain remarkably smaller amounts of sugars as compared with conventional lyophilized formulations or they contain substantially no sugars.

Preferably, the formulations of the present invention substantially consist of the following components:
A) an antibody,
B) one or more amino acid selected from the group consisting of arginine, histidine, lysine, serine, proline, glycine, alanine, threonine and salts thereof,
C) a salt as a buffer, and
D) a surfactant.

"Substantially consist of" means that the formulations do not contain any component other than the optional additives described below as commonly contained in formulations such as suspending agents, solubilizers, isotonizing agents, preservatives, adsorption inhibitors, diluents, fillers, pH modifiers, soothing agents, sulfur-containing reducing agents, antioxidants, etc.

When a formulation of the present invention is to be prepared, an amino acid selected from the group consisting of arginine, histidine, lysine, serine, proline, glycine, alanine, threonine and salts thereof is added to a prepared solution containing an antibody before lyophilization and then the solution is lyophilized. Thus, a good lyophilized cake is formed without using sugars conventionally used as fillers, and at the same time, the production of dimers of the antibody can be inhibited during the lyophilization process.

The present invention also provides an antibody-containing lyophilized formulation including one or more amino acid selected from the group consisting of arginine, histidine, lysine, serine, proline, glycine, alanine and threonine or a salt thereof as a lyoprotectant or a filler characterized in that it includes 25 mg/ml or more of the amino acid or a salt thereof when the antibody concentration of the lyophilized formulation is 20 mg/mL or more, or it includes 12.5 mg/ml or more of the amino acid or a salt thereof when the antibody concentration is 30 mg/mL or more, or it includes 6.25 mg/ml or more of the amino acid or a salt thereof when the antibody concentration is 40 mg/mL or more. Preferably, it includes 25 mg/ml or more of the amino acid or a salt thereof when the antibody concentration of the lyophilized formulation is 30 mg/mL or more, or it includes 12.5 mg/ml or more of the amino acid or a salt thereof when the antibody concentration is 40 mg/mL or more.

The present invention also provides a process for preparing an antibody-containing lyophilized formulation including one or more amino acid selected from the group consisting of arginine, histidine, lysine, serine, proline, glycine, alanine and threonine or a salt thereof as a lyoprotectant or a filler, comprising the step of lyophilizing a solution before lyophilization having a total concentration of reducing sugars, non-reducing sugars, sugar alcohols and polysaccharides of less than 20 mg/mL. The total concentration of reducing sugars, non-reducing sugars, sugar alcohols or polysaccharides is preferably 10 mg/mL or less, more preferably 5 mg/mL or less, still more preferably 1 mg/mL or less, especially substantially zero.

Typical examples of surfactants include:
nonionic surfactants, e.g., sorbitan fatty acid esters such as sorbitan monocaprylate, sorbitan monolaurate, sorbitan monopalmitate; glycerin fatty acid esters such as glycerin monocaprylate, glycerin monomyristate, glycerin monostearate; polyglycerin fatty acid esters such as decaglyceryl monostearate, decaglyceryl distearate, decaglyceryl monolinoleate; polyoxyethylene sorbitan fatty acid esters such as polyoxyethylene sorbitan monolaurate, polyoxyethylene sorbitan monooleate, polyoxyethylene sorbitan monostearate, polyoxyethylene sorbitan monopalmitate, polyoxyethylene sorbitan trioleate, polyoxyethylene sorbitan tristearate; polyoxyethylene sorbitol fatty acid esters such as polyoxyethylene sorbitol tetrastearate, polyoxyethylene sorbitol tetraoleate; polyoxyethylene glycerin fatty acid esters such as polyoxyethylene glyceryl monostearate; polyethylene glycol fatty acid esters such as polyethylene glycol distearate; polyoxyethylene alkyl ethers such as polyoxyethylene lauryl ether; polyoxyethylene polyoxypropylene alkyl ethers such as polyoxyethylene polyoxypropylene glycol ether, polyoxyethylene polyoxypropylene propyl ether, polyoxyethylene polyoxypropylene cetyl ether; polyoxyethylene alkyl phenyl ethers such as polyoxyethylene nonyl phenyl ether; polyoxyethylene hardened castor oils such as polyoxyethylene castor oil, polyoxyethylene hardened castor oil (polyoxyethylene hydrogenated castor oil); polyoxyethylene beeswax derivatives such as polyoxyethylene sorbitol beeswax; polyoxyethylene lanolin derivatives such as polyoxyethylene lanolin; polyoxyethylene fatty acid amides such as polyoxyethylene stearic acid amide having an HLB of 6-18;

anionic surfactants, e.g., alkyl sulfates having a C10-18 alkyl group such as sodium cetyl sulfate, sodium lauryl sulfate, sodium oleyl sulfate; polyoxyethylene alkyl ether sulfates having an average EO mole number of 2-4 and a C10-18 alkyl group such as sodium polyoxyethylene lauryl sulfate; alkyl sulfosuccinic acid ester salts having a C8-18 alkyl group such as sodium laurylsulfosuccinate; and natural surfactants, e.g., lecithin; glycerophospholipids; sphingophospholipids such as sphingomyelin; sucrose fatty acid esters of C12-18 fatty acids. Formulations of the present invention can contain one or more of these surfactants in combination.

Preferred surfactants are polyoxyethylene sorbitan fatty acid esters and polyoxyethylene polyoxypropylene alkyl ethers, more preferably Polysorbates 20, 21, 40, 60, 65, 80, 81, 85 and Pluronic surfactants, most preferably Polysorbates 20 and 80 and Pluronic F-68 (poloxamer 188).

The amount of surfactants to be added to the antibody formulations of the present invention is typically 0.0001-10% (w/v), preferably 0.001-5%, more preferably 0.005-3%.

Salts that can be used as buffers include inorganic salts such as sodium phosphate, potassium phosphate and sodium bicarbonate; and organic salts such as sodium citrate, potassium citrate and sodium acetate. Acids that can be used as buffers include phosphoric acid, carbonic acid, citric acid, succinic acid, malic acid, etc. Other buffers that can be used include Tris buffers and Good's buffers such as MES and MOPS.

The formulations of the present invention can contain suspending agents, solubilizers, isotonizing agents, preservatives, adsorption inhibitors, diluents, fillers, pH modifiers, soothing agents, sulfur-containing reducing agents, antioxidants, etc., if desired.

Examples of suspending agents include methylcellulose, Polysorbate 80, hydroxyethylcellulose, gum acacia, tragacanth powder, sodium carboxymethylcellulose, polyoxyethylene sorbitan monolaurate, etc.

Solubilizers include polyoxyethylene hydrogenated castor oil, Polysorbate 80, nicotinic acid amide, polyoxyethylene sorbitan monolaurate, Macrogols, castor oil fatty acid ethyl esters, etc.

Isotonizing agents include e.g., sodium chloride, potassium chloride, calcium chloride, etc.

Preservatives include e.g., methyl paraoxybenzoate, ethyl paraoxybenzoate, sorbic acid, phenol, cresol, chlorocresol, etc.

Adsorption inhibitors include e.g., human serum albumin, lecithin, dextran, ethylene oxide/propylene oxide copolymers, hydroxypropylcellulose, methylcellulose, polyoxyethylene hydrogenated castor oil, polyethylene glycol, etc.

Sulfur-containing reducing agents include e.g., N-acetylcysteine, N-acetylhomocysteine, thioctic acid, thiodiglycol, thioethanolamine, thioglycerol, thiosorbitol, thioglycolic acid and salts thereof, sodium thiosulfate, glutathione, and sulfhydryl-containing compounds such as thioalkanoic acid having 1 to 7 carbon atoms.

Antioxidants include e.g., erythorbic acid, dibutylhydroxytoluene, butylhydroxyanisole, α-tocopherol, tocopherol acetate, L-ascorbic acid and salts thereof, L-ascorbyl palmitate, L-ascorbyl stearate, sodium bisulfite, sodium sulfite, triamyl gallate, propyl gallate or chelating agents such as disodium ethylenediamine tetraacetate (EDTA), sodium pyrophosphate and sodium metaphosphate.

The antibody-containing lyophilized formulations of the present invention are normally administered via parenteral routes, for example by injection (e.g. subcutaneous, intravenous or intramuscular injection) or via percutaneous, mucosal, nasal or pulmonary route, but can also be orally administered. The formulations of the present invention are especially suitable for subcutaneous injection because the injectable volume is normally limited despite of a single high antibody dose (about 100-200 mg).

As shown from the results of the examples below, the formulations of the present invention can provide good lyophilized compositions without using sugars conventionally used as fillers by adding a specific amino acid, thereby reducing the viscosity of the solution after reconstitution, which was an issue especially when high-concentration antibody-containing formulations are prepared by means of lyophilization-based concentration. Moreover, stable antibody formulations that form little dimers or low molecular weight degradation products of the antibody during the lyophilization process and during storage and reconstitution of the resulting high-concentration lyophilized formulations can be obtained.

Although the present invention has been illustrated in terms of antibodies, which are the most preferred embodiment, the present invention is not limited to such antibodies and is also applicable to other proteins. Proteins used in the formulations of the present invention include, but not limited to, hematopoietic factors such as granulocyte colony-stimulating factor (G-CSF), granulocyte-macrophage colony-stimulating factor (GM-CSF), erythropoietin (EPO) and thrombopoietin, cytokines such as interferon, IL-1 and IL-6, as well as tissue plasminogen activator (TPA), urokinase, serum albumin, blood coagulation factor VIII, leptin, insulin, stem cell factor (SCF), etc.

The following examples further illustrate the present invention without, however, limiting the scope of the invention thereto. Various changes and modifications can be made by those skilled in the art on the basis of the description herein, and such changes and modifications are also included in the present invention.

EXAMPLES

Antibody Sample

A humanized anti-IL-6 receptor antibody was prepared by the method described in Reference example 2 of JPA No. HEI-8-99902 using the human elongation factor Iα promoter described in Example 10 of International Publication No. WO 92/19759. It is sometimes referred to as MRA in the tables in the examples below.

Example 1

Selection of Filler Types Having the Effect of Stabilizing Lyophilized Formulations Filler types having the effect of stabilizing lyophilized formulations containing the humanized anti-IL-6 receptor antibody were sought with the aim of stabilizing them before and after the lyophilization process and on storage.

In this study, evaluation samples of sample Nos. 1-11 were prepared to evaluate the effect of adding the following ten fillers. The formulae of the prepared solutions of the evaluation samples before lyophilization are as follows.

[Formulae of prepared solutions (before lyophilization)]

| Sample No. | Anti- body mg/mL | Filler Type | Content (mg/mL) | Polysorbate 80 mg/mL | Phosphate buffer mM | pH |
|---|---|---|---|---|---|---|
| 1 | 40 | Sucrose | 25 | 0.5 | 15 | 7.0 |
| 2 | 40 | Trehalose | 25 | 0.5 | 15 | 7.0 |
| 3 | 40 | Raffinose | 25 | 0.5 | 15 | 7.0 |
| 4 | 40 | Mannitol | 25 | 0.5 | 15 | 7.0 |
| 5 | 40 | Dextran | 25 | 0.5 | 15 | 7.0 |
| 6 | 40 | Arginine | 25 | 0.5 | 15 | 7.0 |
| 7 | 40 | Histidine | 25 | 0.5 | 15 | 7.0 |
| 8 | 40 | Glycine | 25 | 0.5 | 15 | 7.0 |
| 9 | 40 | Serine | 25 | 0.5 | 15 | 7.0 |
| 10 | 40 | Proline | 25 | 0.5 | 15 | 7.0 |
| 11 | 40 | — | — | 0.5 | 15 | 7.0 |

A glass vial containing 2 mL of the prepared solution of each evaluation sample was lyophilized under the following conditions to give a lyophilized formulation.

Lyophilization conditions

| Step | Shelf temperature | Period | Degree of vacuum |
|---|---|---|---|
| Initial freezing | −50° C. | ca. 24 hr | — |
| Primary drying | −20° C. | 70 hr | 10 Pa |
| Secondary drying (1) | 25° C. | 28 hr | 6 Pa |
| Secondary drying (2) | 30° C. | 10 hr | 6 Pa |

The formulae of the lyophilized formulations of the evaluations samples are as follows.

[Formulae of lyophilized formulations (after lyophilization)]

| Sample No. | Anti- body mg/vial | Filler Type | Content (mg/vial) | Polysorbate 80 mg/vial | Phosphate buffer μmol/vial | pH |
|---|---|---|---|---|---|---|
| 1 | 80 | Sucrose | 50 | 1 | 30 | 7.0 |
| 2 | 80 | Trehalose | 50 | 1 | 30 | 7.0 |
| 3 | 80 | Raffinose | 50 | 1 | 30 | 7.0 |
| 4 | 80 | Mannitol | 50 | 1 | 30 | 7.0 |
| 5 | 80 | Dextran | 50 | 1 | 30 | 7.0 |
| 6 | 80 | Arginine | 50 | 1 | 30 | 7.0 |
| 7 | 80 | Histidine | 50 | 1 | 30 | 7.0 |
| 8 | 80 | Glycine | 50 | 1 | 30 | 7.0 |
| 9 | 80 | Serine | 50 | 1 | 30 | 7.0 |
| 10 | 80 | Proline | 50 | 1 | 30 | 7.0 |
| 11 | 80 | — | — | 1 | 30 | 7.0 |

In order to evaluate stability during the lyophilization process, the purity of each sample of the prepared solutions before lyophilization and the lyophilized formulations after lyophilization was evaluated by gel filtration chromatography (SEC) and ion exchange chromatography (IEC). The assay conditions are as follows.

[Gel Filtration Chromatography]

The samples of the prepared solutions and the lyophilized formulations after lyophilization are assayed as solutions prepared by adding a phosphate buffer at pH 7.0 to each sample to contain the humanized anti-IL-6 receptor antibody in an amount equivalent to about 1 mg/mL.

The samples of the lyophilized formulations on storage are assayed as solutions prepared by adding 0.6 mL/vial of purified water to each formulation.

The assay solution of each sample is tested under the following assay conditions to determine the component levels (%) of dimers (Dimer) and low molecular weight degradation products (LMW) in relation to the total peak components. In some samples that were found to form aggregates having molecular weights higher than those of dimers, the total amount of the aggregates and dimers was reported as dimer level (%).

Assay Conditions

Column: TSK gel G3000SWxl 7.8 mm I.D.×30 cm (TOSOH).

Mobile phase: phosphate buffer, pH 7.0 (50 mmol/L phosphate buffer, pH7.0, containing 300 mmol/L sodium chloride and 0.05% sodium azide).

Sample amount injected: about 60-120 μg expressed as the amount of the humanized anti-IL-6 receptor antibody.

Flow rate: 1 mL/min.

Detected at wavelength: 280 nm.

[Ion Exchange Chromatography]

The samples of the prepared solutions and the lyophilized formulations after lyophilization are assayed as solutions prepared by adding purified water to each sample to contain the humanized anti-IL-6 receptor antibody in an amount equivalent to about 1 mg/mL.

The samples of the lyophilized formulations on storage are assayed as solutions prepared by adding 0.6 mL/vial of purified water to each formulation.

The assay solution of each sample is tested under the following assay conditions to determine the component levels (%) of prepeaks (the sum of peaks eluted at retention times shorter than that of the major component) in relation to the total peak components. The prepeaks include multiple decomposition products mainly consisting of deamidation products of the humanized anti-IL-6 receptor antibody, and low prepeak production levels mean that the deamidation of the antibody was inhibited.

Assay Conditions

Column: PolyCAT A 10 cm×4.6 mm, particle size 3 μm, pore diameter 150 nm (PolyLC).

Mobile phase: Solution A: 25 mmol/L MES buffer, pH 6.1. Solution B: 25 mmol/L MES buffer, pH 6.1 (containing 250 mM sodium acetate).

Sample amount injected: about 30-120 μg expressed as the amount of the humanized anti-IL-6 receptor antibody.

Flow rate: 1 mL/min

Detected at wavelength: 280 nm.

The evaluation results are shown in Table 1. Thus, inhibitory effects against dimer formation could be observed in the samples containing arginine (sample No. 6), histidine (sample No. 7), serine (sample No. 9) and proline (sample No. 10), as shown by obvious reduction in the increase in dimer level after lyophilization. These effects were higher than those obtained with sucrose or trehalose known as typical lyoprotectant. All the samples showed almost no low molecular weight degradation products. In Table 1, Dimer represents dimers, LMW represents low molecular weight degradation products, and Pre represents the sum of peaks eluted at retention times shorter than that of the major component.

TABLE 1

| Sample No. | Dimer (%) | | | LMW (%) | | MRA Pre (%) | | |
|---|---|---|---|---|---|---|---|---|
| | Prepared solution | After lyophilization | (Increase) | Prepared solution | After lyophilization | Prepared solution | After lyophilization | (Increase) |
| 1 | 0.42 | 0.58 | 0.16 | 0.00 | 0.00 | 17.4 | 17.0 | −0.4 |
| 2 | 0.32 | 0.54 | 0.22 | 0.00 | 0.05 | — | — | — |
| 3 | 0.33 | 0.58 | 0.25 | 0.00 | 0.00 | — | — | — |
| 4 | 0.42 | 1.05 | 0.63 | 0.00 | 0.00 | 17.6 | 17.6 | 0.0 |
| 5 | 0.60 | 8.37 | 7.77 | 0.00 | 0.00 | 17.6 | 21.3 | 3.7 |
| 6 | 0.35 | 0.36 | 0.01 | 0.00 | 0.00 | 17.0 | 17.0 | 0.0 |
| 7 | 0.70 | 0.68 | −0.02 | 0.00 | 0.00 | 17.0 | 16.4 | −0.6 |
| 8 | 0.33 | 2.84 | 2.51 | 0.00 | 0.00 | 17.3 | 18.2 | 0.9 |
| 9 | 0.33 | 0.35 | 0.02 | 0.00 | 0.00 | 17.7 | 17.7 | 0.0 |
| 10 | 0.38 | 0.45 | 0.07 | 0.00 | 0.00 | 17.5 | 17.7 | 0.2 |
| 11 | 0.35 | 1.86 | 1.51 | 0.00 | 0.07 | — | — | — |

Then, a thermal acceleration test (storage at 40° C. for 1 month) was performed on each sample to evaluate the stability of the lyophilized formulations on storage. The purity of the antibody before and after thermal acceleration was evaluated by SEC and IEC. The assay conditions are as described above.

The evaluation results are shown in Table 2. Thus, inhibitory effects against dimer formation could be observed in the samples containing arginine (sample No. 6), histidine (sample No. 7), serine (sample No. 9) and proline (sample No. 10), as shown by the increase in dimer level of less than 1% after acceleration at 40° C. for one month. All the samples showed almost no production of low molecular weight degradation products. The samples containing sucrose (sample No. 1), trehalose (sample No. 2), raffinose (sample No. 3), mannitol (sample No. 4), arginine (sample No. 6), histidine (sample No. 7), serine (sample No. 9) and proline (sample No. 10) showed almost no increase in prepeaks by IEC analysis.

TABLE 2

| Sample No. | Dimer (%) | | | LMW (%) | | MRA Pre (%) | | |
|---|---|---|---|---|---|---|---|---|
| | Initial | 40° C.-1 M | (increase) | Initial | 40° C.-1 M | Initial | 40° C.-1 M | (increase) |
| 1 | 0.82 | 2.92 | 2.10 | 0.00 | 0.07 | 17.3 | 18.3 | 1.0 |
| 2 | 0.87 | 4.06 | 3.19 | 0.05 | 0.00 | 16.8 | 18.0 | 1.2 |
| 3 | 0.96 | 4.67 | 3.71 | 0.00 | 0.00 | 16.8 | 18.8 | 2.0 |
| 4 | 1.24 | 4.06 | 2.82 | 0.00 | 0.00 | 17.4 | 18.5 | 1.1 |
| 5 | 8.72 | 38.89 | 30.17 | 0.00 | 0.00 | 21.3 | 37.5 | 16.2 |
| 6 | 0.42 | 0.97 | 0.55 | 0.00 | 0.00 | 17.0 | 17.2 | 0.2 |
| 7 | 0.72 | 1.19 | 0.47 | 0.00 | 0.00 | 16.7 | 16.8 | 0.1 |
| 8 | 2.93 | 10.09 | 7.16 | 0.00 | 0.12 | 17.9 | 22.6 | 4.7 |
| 9 | 0.40 | 1.32 | 0.92 | 0.00 | 0.00 | 17.8 | 19.0 | 1.2 |
| 10 | 0.56 | 1.69 | 1.13 | 0.00 | 0.00 | 17.6 | 18.8 | 1.2 |
| 11 | 2.76 | 18.31 | 15.55 | 0.07 | 0.00 | 17.2 | 23.0 | 5.8 |

Example 2

Influence of the Amounts of Arginine and Sucrose Added to Lyophilized Formulations on Stability The influence of the amounts of arginine and sucrose added to lyophilized formulations containing the humanized anti-IL-6 receptor antibody on the stabilization before and after the lyophilization process and on storage was evaluated.

In this study, evaluation samples of sample Nos. 12-17 containing arginine and sucrose each at three levels were prepared. The formulae of the prepared solutions of the evaluation samples before lyophilization are as follows.

[Formulae of prepared solutions (before lyophilization)]

| Sample No. | Antibody mg/mL | Sucrose mg/mL | Arginine mg/mL | Polysorbate 80 mg/mL | Phosphate buffer mM | pH |
|---|---|---|---|---|---|---|
| 12 | 40 | — | 25 | 0.5 | 15 | 6.0 |
| 13 | 40 | — | 17.5 | 0.5 | 15 | 6.0 |
| 14 | 40 | — | 12.5 | 0.5 | 15 | 6.0 |
| 15 | 40 | 50 | — | 0.5 | 15 | 6.0 |
| 16 | 40 | 35 | — | 0.5 | 15 | 6.0 |
| 17 | 40 | 25 | — | 0.5 | 15 | 6.0 |

A glass vial containing 2 mL of the prepared solution of each evaluation sample was lyophilized under the conditions similar to those of Example 1 to give a lyophilized formulation. The formulae of the lyophilized formulations of the evaluations samples are as follows.

[Formulae of lyophilized formulations (after lyophilization)]

| Sample No. | Antibody mg/vial | Sucrose mg/vial | Arginine mg/vial | Polysorbate 80 mg/vial | Phosphate buffer μmol/vial | pH |
|---|---|---|---|---|---|---|
| 12 | 80 | — | 50 | 1 | 30 | 6.0 |
| 13 | 80 | — | 35 | 1 | 30 | 6.0 |
| 14 | 80 | — | 25 | 1 | 30 | 6.0 |
| 15 | 80 | 100 | — | 1 | 30 | 6.0 |
| 16 | 80 | 70 | — | 1 | 30 | 6.0 |
| 17 | 80 | 50 | — | 1 | 30 | 6.0 |

In order to evaluate stability during the lyophilization process, the purity of each sample of the prepared solutions before lyophilization and the lyophilized formulations after lyophilization was evaluated by SEC and IEC in the same manner as in Example 1.

The evaluation results are shown in Table 3. Inhibitory effects against dimer formation could be observed after lyophilization in the samples containing arginine at 17.5 mg/mL (sample No. 13) or more. On the other hand, similar effects could be observed in only the sample containing sucrose at 50 mg/mL (sample No. 14) or more. Thus, it could be found that arginine has a better stabilizing effect after lyophilization than sucrose. It should be noted that the molar concentration of sucrose in sample No. 15 is equal to the molar concentration of arginine in sample No. 12. In the all samples, neither low molecular weight degradation products nor increase in prepeaks (IEC) was observed.

TABLE 3

| Sample No. | Dimer (%) | | | LMW (%) | | MRA Pre (%) | | |
|---|---|---|---|---|---|---|---|---|
| | Prepared solution | After lyophilization | (Increase) | Prepared solution | After lyophilization | Prepared solution | After lyophilization | (Increase) |
| 12 | 0.34 | 0.32 | −0.02 | 0.00 | 0.00 | 16.5 | 17.1 | 0.6 |
| 13 | 0.37 | 0.39 | 0.02 | 0.00 | 0.00 | 16.6 | 17.2 | 0.6 |
| 14 | 0.36 | 0.42 | 0.06 | 0.00 | 0.00 | 16.8 | 17.2 | 0.4 |
| 15 | 0.45 | 0.48 | 0.03 | 0.00 | 0.00 | 17.1 | 17.3 | 0.2 |
| 16 | 0.48 | 0.55 | 0.07 | 0.00 | 0.00 | 17.2 | 17.8 | 0.6 |
| 17 | 0.50 | 0.66 | 0.16 | 0.00 | 0.00 | 16.9 | 17.5 | 0.6 |

Then, a thermal acceleration test (storage at 40° C. and 25° C. for 1 month) was performed on each sample to evaluate the stability of the lyophilized formulations on storage. The purity of the antibody before and after thermal acceleration was evaluated by SEC and IEC in the same manner as in Example 1.

Evaluation results are shown in Table 4. The inhibitory effects of both arginine and sucrose against dimer formation after acceleration at 40° C. and 25° C. for one month increased as the contents increased. However, arginine showed slightly lower increase in dimer level at low contents. At any content, almost no low molecular weight degradation products were observed and no increase in prepeaks (IEC) was observed.

Example 3

Influence of the pH of Lyophilized Formulations Containing Arginine on Stability The influence of the pH of lyophilized formulations containing the humanized anti-IL-6 receptor antibody and arginine on the stabilization before and after the lyophilization process and on storage was evaluated.

In this study, evaluation samples of sample Nos. 18-21 having a formulation pH in the range of 5.5-7.0 were prepared. The formulae of the prepared solutions of the evaluation samples before lyophilization are as follows.

[Formulae of prepared solutions (before lyophilization)]

| Sample No. | Antibody mg/mL | Arginine mg/mL | Polysorbate 80 mg/mL | Phosphate buffer mM | pH |
|---|---|---|---|---|---|
| 18 | 40 | 25 | 0.5 | 15 | 7.0 |
| 19 | 40 | 25 | 0.5 | 15 | 6.5 |
| 20 | 40 | 25 | 0.5 | 15 | 6.0 |
| 21 | 40 | 25 | 0.5 | 15 | 5.5 |

A glass vial containing 2 mL of the prepared solution of each evaluation sample was lyophilized under the conditions similar to those of Example 1 to give a lyophilized formula-

TABLE 4

| Sample No. | Dimer (%) | | | | | LMW (%) | | |
|---|---|---|---|---|---|---|---|---|
| | Initial | 40° C.-1 M | (Increase) | 25° C.-1 M | (Increase) | Initial | 40° C.-1 M | 25° C.-1 M |
| 12 | 0.31 | 0.82 | 0.51 | 0.47 | 0.16 | 0.00 | 0.11 | 0.00 |
| 13 | 0.37 | 1.15 | 0.78 | 0.60 | 0.23 | 0.00 | 0.06 | 0.00 |
| 14 | 0.41 | 1.66 | 1.25 | 0.73 | 0.32 | 0.00 | 0.13 | 0.00 |
| 15 | 0.53 | 1.07 | 0.54 | 0.69 | 0.16 | 0.00 | 0.00 | 0.00 |
| 16 | 0.64 | 1.63 | 0.99 | 0.89 | 0.25 | 0.00 | 0.00 | 0.00 |
| 17 | 0.70 | 2.27 | 1.57 | 1.12 | 0.42 | 0.00 | 0.00 | 0.00 |

| Sample No. | MRA Pre (%) | | | | |
|---|---|---|---|---|---|
| | Initial | 40° C.-1 M | (Increase) | 25° C.-1 M | (Increase) |
| 12 | 16.8 | 16.8 | 0.0 | 16.7 | −0.1 |
| 13 | 16.7 | 17.1 | 0.4 | 16.8 | 0.1 |
| 14 | 16.7 | 17.2 | 0.5 | 16.7 | 0.0 |
| 15 | 17.2 | 17.5 | 0.3 | 17.1 | −0.1 |
| 16 | 17.1 | 17.7 | 0.6 | 17.1 | 0.0 |
| 17 | 17.0 | 18.0 | 1.0 | 17.4 | 0.4 | tion. The formulae of the lyophilized formulations of the evaluations samples are as follows.

[Formulae of lyophilized formulations (after lyophilization)]

| Sample No. | Antibody mg/vial | Arginine mg/vial | Polysorbate 80 mg/vial | Phosphate buffer μmol/vial | pH |
|---|---|---|---|---|---|
| 18 | 80 | 50 | 1 | 30 | 7.0 |
| 19 | 80 | 50 | 1 | 30 | 6.5 |
| 20 | 80 | 50 | 1 | 30 | 6.0 |
| 21 | 80 | 50 | 1 | 30 | 5.5 |

In order to evaluate stability during the lyophilization process, the purity of each sample of the prepared solutions before lyophilization and the lyophilized formulations after lyophilization was evaluated by SEC and IEC in the same manner as in Example 1.

The evaluation results are shown in Table 5. The dimer levels in the prepared solutions decreased as the pH decreased, but no dimer formation was observed at any pH after lyophilization. In the all samples, neither low molecular weight degradation products nor increase in prepeaks (IEC) was observed.

TABLE 5

| Sample No. | Dimer (%) | | | LMW (%) | | MRA Pre (%) | | |
|---|---|---|---|---|---|---|---|---|
| | Prepared solution | After lyophilization | (Increase) | Prepared solution | After lyophilization | Prepared solution | After lyophilization | (Increase) |
| 18 | 0.42 | 0.44 | 0.02 | 0.00 | 0.00 | 16.5 | 17.2 | 0.7 |
| 19 | 0.36 | 0.35 | −0.01 | 0.00 | 0.00 | 16.9 | 17.3 | 0.4 |
| 20 | 0.34 | 0.32 | −0.02 | 0.00 | 0.00 | 16.5 | 17.1 | 0.6 |
| 21 | 0.35 | 0.32 | −0.03 | 0.00 | 0.00 | 17.5 | 16.6 | −0.9 |

Then, a thermal acceleration test (storage at 40° C. and 25° C. for 1 month) was performed on each sample to evaluate the stability of the lyophilized formulations on storage. The purity of the antibody before and after thermal acceleration was evaluated by SEC and IEC in the same manner as in Example 1.

The evaluation results are shown in Table 6. Depending on the dimer levels of the prepared solutions, the dimer levels before acceleration decreased as the pH decreased. However, the increase in dimer level was comparable at any pH after acceleration at 40° C. and 25° C. for one month. At any pH, almost no low molecular weight degradation products were observed and no increase in prepeaks (IEC) was observed.

TABLE 6

| Sample No. | Dimer (%) | | | | | LMW (%) | | |
|---|---|---|---|---|---|---|---|---|
| | Initial | 40° C.-1 M | (Increase) | 25° C.-1 M | (Increase) | Initial | 40° C.-1 M | 25° C.-1 M |
| 18 | 0.44 | 0.95 | 0.51 | 0.61 | 0.17 | 0.00 | 0.00 | 0.00 |
| 19 | 0.34 | 0.82 | 0.48 | 0.50 | 0.16 | 0.00 | 0.05 | 0.00 |
| 20 | 0.31 | 0.82 | 0.51 | 0.47 | 0.16 | 0.00 | 0.11 | 0.00 |
| 21 | 0.31 | 0.82 | 0.51 | 0.47 | 0.16 | 0.00 | 0.05 | 0.00 |

| Sample No. | MRA Pre (%) | | | | |
|---|---|---|---|---|---|
| | Initial | 40° C.-1 M | (Increase) | 25° C.-1 M | (Increase) |
| 18 | 17.0 | 17.2 | 0.2 | 17.0 | 0.0 |
| 19 | 16.8 | 17.0 | 0.2 | 16.9 | 0.1 |
| 20 | 16.8 | 16.8 | 0.0 | 16.7 | −0.1 |
| 21 | 16.5 | 16.6 | 0.1 | 16.5 | 0.0 |

Example 4

Influence of the Antibody Content in Lyophilized Formulations Containing Arginine on Stability In order to determine the possibility of enrichment of lyophilized formulations containing the humanized anti-IL-6 receptor antibody and arginine, the influence of the antibody content on the stabilization of the formulations before and after the lyophilization process and on storage was evaluated.

In this study, evaluation samples of sample Nos. 22-23 containing 80 and 240 mg/vial of the antibody in the formulations were prepared. The formulae of the prepared solutions of the evaluation samples before lyophilization are as follows.

[Formulae of prepared solutions (before lyophilization)]

| Sample No. | Antibody mg/mL | Arginine mg/mL | Polysorbate 80 mg/mL | Phosphate buffer mM | pH |
|---|---|---|---|---|---|
| 22 | 40 | 25 | 0.5 | 15 | 6.0 |
| 23 | 40 | 25 | 0.5 | 15 | 6.0 |

A glass vial containing 2 mL of the prepared solution of sample No. 22 or 6 mL of the prepared solution of sample No. 23 was lyophilized under the following conditions to give a lyophilized formulation.

| Lyophilization conditions | | | |
|---|---|---|---|
| Step | Shelf temperature | Period | Degree of vacuum |
| Initial freezing | −50° C. | ca. 24 hr | — |
| Primary drying | −20° C. | 105 hr | 10 Pa |
| Secondary drying (1) | 25° C. | 28 hr | 6 Pa |
| Secondary drying (2) | 30° C. | 10 hr | 6 Pa |

The formulae of the lyophilized formulations of the evaluations samples are as follows.

[Formulae of lyophilized formulations (after lyophilization)]

| Sample No. | Antibody mg/vial | Arginine mg/vial | Polysorbate 80 mg/vial | Phosphate buffer μmol/vial | pH |
|---|---|---|---|---|---|
| 22 | 80 | 50 | 1 | 30 | 6.0 |
| 23 | 240 | 150 | 3 | 90 | 6.0 |

In order to evaluate stability during the lyophilization process, the purity of each sample of the prepared solutions before lyophilization and the lyophilized formulations after lyophilization was evaluated by SEC in the same manner as in Example 1.

The evaluation results are shown in Table 7. At any content, neither increase in dimer level after lyophilization nor low molecular weight degradation products were observed.

TABLE 7

| | Dimer (%) | | | LMW (%) | |
|---|---|---|---|---|---|
| Sample No. | Prepared solution | After lyophilization | (Increase) | Prepared solution | After lyophilization |
| 22 | 0.34 | 0.32 | −0.02 | 0.00 | 0.00 |
| 23 | 0.46 | 0.43 | −0.03 | 0.00 | 0.00 |

Then, a thermal acceleration test (storage at 40° C. and 25° C. for 1 month) was performed on each sample to evaluate the stability of the lyophilized formulations on storage. The purity of the antibody before and after thermal acceleration was evaluated by SEC in the same manner as in Example 1.

The evaluation results are shown in Table 8. The increase in dimer level was comparable at any content after acceleration at 40° C. and 25° C. for one month. At any content, almost no low molecular weight degradation products were observed.

TABLE 8

| Sample No. | Dimer (%) | | | | | LMW (%) | | |
|---|---|---|---|---|---|---|---|---|
| | Initial | 40° C.-1 M | (Increase) | 25° C.-1 M | (Increase) | Initial | 40° C.-1 M | 25° C.-1 M |
| 22 | 0.31 | 0.82 | 0.51 | 0.47 | 0.16 | 0.00 | 0.11 | 0.00 |
| 23 | 0.43 | 0.97 | 0.54 | 0.61 | 0.18 | 0.00 | 0.00 | 0.00 |

Example 5

Selection of the Types and Contents of Fillers on the Basis of the Quality of Lyophilized Cakes of Lyophilized Formulations To determine the influence of filler types on the quality of lyophilized cakes of lyophilized formulations containing the humanized anti-IL-6 receptor antibody, the samples evaluated in Example 1 (sample Nos. 1-11) were visually evaluated for the presence of shrinkage in lyophilized cakes. Samples showing shrinkage of 1 mm or more in radius in lyophilized cakes were assessed as "shrinkage".

The results are shown in Table 9. The sample containing no filler showed a shrinking tendency in the lyophilized cake. However, all the samples containing fillers except for dextran showed no shrinking tendency in the lyophilized cakes and good cake forms.

TABLE 9

| Sample No. | MRA mg/vial | Filler Type | Content (mg/vial) | Polysorbate 80 mg/vial | Phosphate buffer μmol/vial | pH | Cake form |
|---|---|---|---|---|---|---|---|
| 1 | 80 | Sucrose | 50 | 1 | 30 | 7.0 | No shrinkage |
| 2 | 80 | Trehalose | 50 | 1 | 30 | 7.0 | No shrinkage |
| 3 | 80 | Raffinose | 50 | 1 | 30 | 7.0 | No shrinkage |
| 4 | 80 | Mannitol | 50 | 1 | 30 | 7.0 | No shrinkage |
| 5 | 80 | Dextran | 50 | 1 | 30 | 7.0 | Shrinkage |
| 6 | 80 | Arginine | 50 | 1 | 30 | 7.0 | No shrinkage |
| 7 | 80 | Histidine | 50 | 1 | 30 | 7.0 | No shrinkage |
| 8 | 80 | Glycine | 50 | 1 | 30 | 7.0 | No shrinkage |
| 9 | 80 | Serine | 50 | 1 | 30 | 7.0 | No shrinkage |
| 10 | 80 | Proline | 50 | 1 | 30 | 7.0 | No shrinkage |
| 11 | 80 | — | — | 1 | 30 | 7.0 | Shrinkage |

Then, the influence of the contents of arginine and sucrose on the quality of lyophilized cakes was evaluated using the samples evaluated in Example 2 (sample Nos. 12-17).

The results are shown in Table 10. The samples containing 50 mg/vial (25 mg/mL in the prepared solutions) or more of arginine or 100 mg/vial (50 mg/mL in the prepared solutions) or more of sucrose showed no shrinking tendency and good lyophilized cake forms.

TABLE 10

| Sample No. | MRA mg/vial | Sucrose mg/vial | Arginine mg/vial | Polysorbate 80 mg/vial | Phosphate buffer μmol/vial | pH | Cake form |
|---|---|---|---|---|---|---|---|
| 12 | 80 | — | 50 | 1 | 30 | 6.0 | No shrinkage |
| 13 | 80 | — | 35 | 1 | 30 | 6.0 | No shrinkage |
| 14 | 80 | — | 25 | 1 | 30 | 6.0 | No shrinkage |
| 15 | 80 | 100 | — | 1 | 30 | 6.0 | No shrinkage |
| 16 | 80 | 70 | — | 1 | 30 | 6.0 | No shrinkage |
| 17 | 80 | 50 | — | 1 | 30 | 6.0 | No shrinkage |

Example 6

Optimization of the Arginine Content on the Basis of the Quality of Lyophilized Cakes of Lyophilized Formulations Containing Arginine The influences of the antibody content and the arginine content on the quality of lyophilized cakes of lyophilized formulations containing the humanized anti-IL-6 receptor antibody and arginine were evaluated.

In this study, evaluation samples of sample Nos. containing 40-160 mg/vial of the antibody in the formulations were prepared. The formulae of the prepared solutions of the evaluation samples before lyophilization are as follows.

[Formulae of prepared solutions (before lyophilization)]

| Sample No. | Antibody mg/mL | Arginine mg/mL | Polysorbate 80 mg/mL | Phosphate buffer mM | pH |
|---|---|---|---|---|---|
| 24 | 20 | 0 | 0.15 | 19 | 6.0 |
| 25 | 20 | 6.25 | 0.15 | 19 | 6.0 |
| 26 | 20 | 12.5 | 0.15 | 19 | 6.0 |
| 27 | 20 | 25 | 0.15 | 19 | 6.0 |
| 28 | 20 | 50 | 0.15 | 19 | 6.0 |
| 29 | 30 | 0 | 0.23 | 19 | 6.0 |
| 30 | 30 | 6.25 | 0.23 | 19 | 6.0 |
| 31 | 30 | 12.5 | 0.23 | 19 | 6.0 |
| 32 | 30 | 25 | 0.23 | 19 | 6.0 |
| 33 | 30 | 50 | 0.23 | 19 | 6.0 |
| 34, 44 | 40 | 0 | 0.31 | 19 | 6.0 |
| 35, 45 | 40 | 6.25 | 0.31 | 19 | 6.0 |
| 36, 46 | 40 | 12.5 | 0.31 | 19 | 6.0 |
| 37, 47 | 40 | 25 | 0.31 | 19 | 6.0 |
| 38, 48 | 40 | 50 | 0.31 | 19 | 6.0 |
| 39 | 60 | 0 | 0.46 | 19 | 6.0 |
| 40 | 60 | 6.25 | 0.46 | 19 | 6.0 |
| 41 | 60 | 12.5 | 0.46 | 19 | 6.0 |
| 42 | 60 | 25 | 0.46 | 19 | 6.0 |
| 43 | 60 | 50 | 0.46 | 19 | 6.0 |

A glass vial containing 2 mL each of the prepared solutions of sample Nos. 24-43 or 4 mL each of the prepared solutions of sample Nos. 44-48 was lyophilized under the conditions similar to those of Example 1 to give ten vials of each lyophilized formulation. The formulae of the lyophilized formulations of the evaluations samples are as follows.

[Formulae of lyophilized formulations (after lyophilization)]

| Sample No. | Antibody mg/vial | Arginine mg/vial | Polysorbate 80 mg/vial | Phosphate buffer μmol/vial | pH |
|---|---|---|---|---|---|
| 24 | 40 | 0 | 0.31 | 38 | 6.0 |
| 25 | 40 | 12.5 | 0.31 | 38 | 6.0 |
| 26 | 40 | 25 | 0.31 | 38 | 6.0 |
| 27 | 40 | 50 | 0.31 | 38 | 6.0 |
| 28 | 40 | 100 | 0.31 | 38 | 6.0 |
| 29 | 60 | 0 | 0.46 | 38 | 6.0 |
| 30 | 60 | 12.5 | 0.46 | 38 | 6.0 |
| 31 | 60 | 25 | 0.46 | 38 | 6.0 |
| 32 | 60 | 50 | 0.46 | 38 | 6.0 |
| 33 | 60 | 100 | 0.46 | 38 | 6.0 |
| 34 | 80 | 0 | 0.61 | 38 | 6.0 |
| 35 | 80 | 12.5 | 0.61 | 38 | 6.0 |
| 36 | 80 | 25 | 0.61 | 38 | 6.0 |
| 37 | 80 | 50 | 0.61 | 38 | 6.0 |
| 38 | 80 | 100 | 0.61 | 38 | 6.0 |
| 39 | 120 | 0 | 0.92 | 38 | 6.0 |
| 40 | 120 | 12.5 | 0.92 | 38 | 6.0 |
| 41 | 120 | 25 | 0.92 | 38 | 6.0 |
| 42 | 120 | 50 | 0.92 | 38 | 6.0 |
| 43 | 120 | 100 | 0.92 | 38 | 6.0 |
| 44 | 160 | 0 | 1.22 | 77 | 6.0 |
| 45 | 160 | 25 | 1.22 | 77 | 6.0 |
| 46 | 160 | 50 | 1.22 | 77 | 6.0 |
| 47 | 160 | 100 | 1.22 | 77 | 6.0 |
| 48 | 160 | 200 | 1.22 | 77 | 6.0 |

Ten vials of each sample were visually evaluated for the presence of shrinkage in lyophilized cakes (by 3 evaluators) in the same manner as in Example 5, and vials showing shrinkage within 1 mm in lyophilized cakes were assessed as conforming, and the percentage of these vials was recorded as percent within limit (PWL). The PWLs of lyophilized cakes of the samples are shown as evaluation results in Table 11.

TABLE 11

| Sample No. | Antibody mg/mL | Arginin mg/mL | Antibody mg/vial | Arginine mg/vial | PWL (%) |
|---|---|---|---|---|---|
| 24 | 20 | 0 | 40 | 0 | 0.0 |
| 25 | 20 | 6.25 | 40 | 12.5 | 0.0 |
| 26 | 20 | 12.5 | 40 | 25 | 13.3 |
| 27 | 20 | 25 | 40 | 50 | 46.7 |
| 28 | 20 | 50 | 40 | 100 | 0.0 |
| 29 | 30 | 0 | 60 | 0 | 0.0 |
| 30 | 30 | 6.25 | 60 | 12.5 | 10.0 |
| 31 | 30 | 12.5 | 60 | 25 | 33.3 |
| 32 | 30 | 25 | 60 | 50 | 63.3 |
| 33 | 30 | 50 | 60 | 100 | 86.7 |
| 34 | 40 | 0 | 80 | 0 | 0.0 |
| 35 | 40 | 6.25 | 80 | 12.5 | 20.0 |
| 36 | 40 | 12.5 | 80 | 25 | 46.7 |
| 37 | 40 | 25 | 80 | 50 | 100.0 |
| 38 | 40 | 50 | 80 | 100 | 100.0 |
| 39 | 60 | 0 | 120 | 0 | 0.0 |
| 40 | 60 | 6.25 | 120 | 12.5 | 13.3 |
| 41 | 60 | 12.5 | 120 | 25 | 53.3 |
| 42 | 60 | 25 | 120 | 50 | 86.7 |
| 43 | 60 | 50 | 120 | 100 | 80.0 |
| 44 | 40 | 0 | 160 | 0 | 6.7 |
| 45 | 40 | 6.25 | 160 | 25 | 16.7 |
| 46 | 40 | 12.5 | 160 | 50 | 53.3 |
| 47 | 40 | 25 | 160 | 100 | 100.0 |
| 48 | 40 | 50 | 160 | 200 | 100.0 |

Samples had substantially no special problem as products if the PWL was 30% or more, preferably 40% or more, more preferably 50% or more in the evaluation results.

Sample Nos. 32, 33, 37, 38, 41, 42, 43, 46, 47, and 48 showed good quality of lyophilized cakes as judged from the proportion of conforming items free from shrinkage in lyophilized cakes of 50% or more. Sample Nos. 33, 37, 38, 42, 43, 47, and 48 showed very good quality of lyophilized cakes as judged from the proportion of conforming items free from shrinkage in lyophilized cakes of 80% or more. Thus, the quality of lyophilized cakes increased as the antibody concentration of the prepared solution increased, and the PWL of lyophilized cakes reached 50% or more by adding 25 mg/mL or more of arginine when the antibody concentration was 30 mg/mL or more. Especially when the antibody concentration was 40 mg/mL or more, the PWL of lyophilized cakes reached 80% or more by adding 25 mg/mL or more of arginine.

Example 7

Influence of the Types of Fillers on the Viscosity of Reconstituted Solutions of Lyophilized Formulations The influence of the types of fillers on the viscosity of reconstituted solutions of lyophilized formulations containing the humanized anti-IL-6 receptor antibody was evaluated.

Reconstituted solutions were prepared by adding 0.6 mL of water for injection to each lyophilized formulation of sample Nos. 1, 2, 3, 6, 8, 9, and 10 among the samples evaluated in Example 1 and used as evaluation samples.

The viscosity of the reconstituted solution of each evaluation sample was measured by using a cone and plate viscometer. The assay conditions are as follows.

[Viscometry]

The viscosity of the reconstituted solution was measured by using a viscoelastometer Rheometer AR-1000 (TA Instruments, Inc.).

| Assay conditions | | |
|---|---|---|
| Geometry: Cone-and-plate system | | |
| (Angle 2°, Diameter 40 mm, Truncation 61 μm) | | |
| Test temperature: 25° C. | | |
| Test cycle: | | |
| Steps | Period | Shear rate |
| Conditioning step | 10 sec | — |
| Continuous ramp step 1 | 5 min | logarithmically increasing from 1 to 300 [1/s] |
| Peak hold step 1 | 15 sec | constant at 300 [1/s] |
| Continuous ramp step 2 | 5 min | logarithmically decreasing from 300 to 1 [1/s] |

The shear stress imposed on the geometry in Continuous ramp step 1 and Continuous ramp step 2 was monitored and the viscosity in each step was calculated from an approximate equation for Newtonian fluids. The average of viscosities in Continuous ramp step 1 and Continuous ramp step 2 was reported as the viscosity of each sample.

The results of viscometry on the samples are shown in Table 12. Formulations containing amino acids as fillers showed lower viscosities than formulations using sugars as fillers at the same content. The formulation containing arginine showed a decrease in viscosity of 1 mPa·s or more as compared with the formulation containing sucrose.

TABLE 12

| Sample No. | Antibody mg/vial | Filler Type | Filler Content mg/vial | Polysorbate 80 mg/vial | Phosphate Buffer μmol/vial | pH | Viscosity mPa·S |
|---|---|---|---|---|---|---|---|
| 1 | 80 | Sucrose | 50 | 1 | 30 | 7 | 3.5 |
| 2 | 80 | Trehalose | 50 | 1 | 30 | 7 | 3.7 |
| 3 | 80 | Raffinose | 50 | 1 | 30 | 7 | 3.7 |
| 6 | 80 | Arginine | 50 | 1 | 30 | 7 | 2.3 |
| 8 | 80 | Glycine | 50 | 1 | 30 | 7 | 3 |
| 9 | 80 | Serine | 50 | 1 | 30 | 7 | 2.7 |
| 10 | 80 | Proline | 50 | 1 | 30 | 7 | 2.9 |

Example 8

Influence of the Antibody Concentration on the Viscosity of Reconstituted Solutions of Lyophilized Formulations Containing Arginine The influence of the antibody concentration on the viscosity of reconstituted solutions of lyophilized formulations containing the humanized anti-IL-6 receptor antibody and arginine was evaluated.

In this study, samples of reconstituted solutions of sample Nos. 49-53 having different antibody concentrations were prepared by varying the amount of water for injection added to sample No. 12 among the samples evaluated in Example 2 as follows. As a reference, a sample of a reconstituted solution (sample No. 54) at an antibody concentration of about 200 mg/mL was prepared from sample No. 16 evaluated in Example 2 consisting of the lyophilized formulation containing the humanized anti-IL-6 receptor antibody and sucrose and measured for viscosity. Viscometry was performed using the same procedure as described in Example 7.

| Sample No. | Antibody mg/mL | Arginine mg/mL | Sucrose mg/mL | Polysorbate 80 mg/mL | Phosphate buffer mM | pH |
|---|---|---|---|---|---|---|
| 49 | 120 | 75 | 0 | 1.5 | 45 | 6.0 |
| 50 | 140 | 87.5 | 0 | 1.75 | 52.5 | 6.0 |
| 51 | 160 | 100 | 0 | 2 | 60 | 6.0 |
| 52 | 180 | 112.5 | 0 | 2.25 | 67.5 | 6.0 |
| 53 | 200 | 125 | 0 | 2.5 | 75 | 6.0 |
| 54 | 195 | 0 | 171 | 2.4 | 73 | 7.0 |

The results of viscometry are shown in Table 13. The viscosity increased with the antibody concentration, but the viscosity at an antibody concentration of 200 mg/mL was 16.9 mPa·s, which was lower than that of the reconstituted solution at an antibody concentration of 195 mg/mL containing sucrose. Thus, the viscosity of the arginine formulation was lower than that of the sucrose formulation at high antibody concentrations despite of the higher molar concentration of arginine, suggesting that arginine may reduce the viscosity of antibody solutions.

TABLE 13

| Sample No. | Antibody mg/mL | Arginine mg/mL | Arginine mM | Sucrose mg/mL | Sucrose mM | Viscosity mPa·S |
|---|---|---|---|---|---|---|
| 49 | 120 | 75 | 431 | 0 | 0 | 3.4 |
| 50 | 140 | 87.5 | 502 | 0 | 0 | 4.9 |
| 51 | 160 | 100 | 574 | 0 | 0 | 7.2 |
| 52 | 180 | 112.5 | 646 | 0 | 0 | 11.0 |
| 53 | 200 | 125 | 718 | 0 | 0 | 16.9 |
| 54 | 195 | 0 | 0 | 171 | 500 | 25.3 |

The invention claimed is:

1. A reconstituted solution obtained by adding water suitable for injection to an antibody-containing lyophilized pharmaceutical formulation free from reducing sugars, non-reducing sugars, sugar alcohols or polysaccharides as fillers and including one or more amino acids selected from the group consisting of arginine, lysine, serine, proline, glycine, alanine and threonine or a salt thereof, wherein the content of the amino acid or a salt thereof is 270 moles or more per mole of the antibody, wherein the antibody concentration in said reconstituted solution is 50 mg/ml or more.

2. The reconstituted solution of claim 1, wherein the pH of the reconstituted solution is 4-8.

3. The reconstituted solution of claim 2, wherein the pH of the reconstituted solution is 5.0-7.5.

4. The reconstituted solution of claim 1, wherein the viscosity of the reconstituted solution is 20 mPa·s or less.

5. The reconstituted solution of claim 4, wherein the viscosity of the reconstituted solution is 15 mPa·s or less.

6. The reconstituted solution of claim 5, wherein the viscosity of the reconstituted solution is 12 mPa·s or less.

* * * * *